United States Patent [19]
Chou

[11] Patent Number: 5,776,158
[45] Date of Patent: *Jul. 7, 1998

[54] PERMANENT PIGMENT APPLICATOR HAVING A DETACHABLE NEEDLE COUPLER

[75] Inventor: Kuei Chun Chou, Taiwan, China

[73] Assignee: Mei-Chi-Na Beauty International, Inc., Irvine, Calif.

[*] Notice: The term of this patent shall not extend beyond the expiration date of Pat. No. 5,472,449.

[21] Appl. No.: 429,724

[22] Filed: Apr. 27, 1995

Related U.S. Application Data

[62] Division of Ser. No. 97,936, Jul. 26, 1993, Pat. No. 5,472,449.

[51] Int. Cl.⁶ .................................................. B43K 5/00
[52] U.S. Cl. .................................................. 606/186; 81/9.22
[58] Field of Search .............................. 606/185–186; 604/181, 187; 81/9.22

[56] References Cited

U.S. PATENT DOCUMENTS

| | | | |
|---|---|---|---|
| 4,204,438 | 5/1980 | Binaris et al. | 30/362 |
| 4,582,060 | 4/1986 | Bailey | 81/9.22 X |
| 4,665,912 | 5/1987 | Burton | 81/9.22 X |
| 4,671,277 | 6/1987 | Beuchat | 81/9.22 X |
| 4,719,825 | 1/1988 | LaHaye et al. | 81/9.22 X |
| 4,796,624 | 1/1989 | Trott et al. | 604/86 X |
| 4,862,772 | 9/1989 | Piperato | 81/9.22 |
| 4,914,988 | 4/1990 | Chang | 81/9.22 |

*Primary Examiner*—Michael Buiz
*Assistant Examiner*—Nancy Connolly Mulcare
*Attorney, Agent, or Firm*—Baker, Maxham, Jester & Meador

[57] ABSTRACT

A device for applying permanent pigment, such as in a tattooing procedure, which has a disposable needle coupler which couples the needle to the device. The device has a housing which is structured to allow easy user access to the internal parts that are likely to be exposed to contamination from the tattooing procedure. The needle coupler is structured to allow easy manipulation to detach it from or attach it to the device without require the use or tools. The pigment applicator device may be a manual device or an electromechanically driven device. In the latter, the needle coupler is detachably coupled to a drive mechanism for actuating reciprocal axial movement of the needle via the needle coupler. The drive mechanism may include a cam for translating a rotational motion into a reciprocal axial motion of the needle coupler.

5 Claims, 2 Drawing Sheets

PERMANENT PIGMENT APPLICATOR HAVING A DETACHABLE NEEDLE COUPLER

This application is a division of application Ser. No. 08/097,936, filed Jul. 26, 1993 now U.S. Pat. No. 5,472,449.

BACKGROUND OF THE INVENTION

1. Field of the Invention

The present invention relates to devices for applying permanent pigment to the skin of a person.

2. Description of Related Art

The marking of a tattoo on a person's skin involves using a needle point applicator to insert color pigments under the skin. The applicator generally includes a handle shaped for a convenient grip by a user's hand, and a metal needle having a sharp pointed tip extending from one end of the handle. The color pigment is applied to the skin by superficially puncturing the skin, and moving the needle in an axial reciprocal motion in and out of the skin to urge the color pigment to just under the skin where the pigment is retained permanently. This procedure inevitably involves exposure of the needle to blood in the body tissues.

In one type of electromechanical tattooing device, the needle is typically supported by the device in a manner to allow it to move axially relative to the device housing/handle. A needle drive mechanism, which can be a motor or other electromagnetic device, actuates the needle in an axial reciprocal manner while the housing is held steady by the user. The needle is detachably coupled to the drive mechanism via a needle coupler within the housing which is not accessible by the user. While the needle is discarded after each use, the needle coupler being an integral part of the device, however, remains attached to the device. It has been experienced that blood from the tattooing procedure can contaminate the needle coupler in the housing which is not accessible by the user for cleaning.

The growing concern of infectious diseases, such as "AIDS" transmitted by blood contaminated with HIV, dictates that special attention must be given to decontaminate between uses on different persons the parts of the applicator device that are exposed to blood from the tattooing procedure. Even if the internal parts of the device such as the needle coupler is accessible by the user, the prior integral construction, however, is not suitable for autoclaving or other types of reliable and acceptable decontamination procedures for blood contamination. Mere wiping off the parts is not acceptable by today's health standards.

SUMMARY OF THE INVENTION

The present invention is directed to a device for applying permanent pigment, such as in a tattooing procedure, which has a disposable needle coupler which couples the needle to the device. The device has a housing which is structured to allow easy user access to the internal parts that are likely to be exposed to contamination from the tattooing procedure. The needle coupler is structured to allow easy manipulation to detach it from or attach it to the device without require the use or tools.

The pigment applicator device may be a manual device or an electro-mechanically driven device. In the latter, the needle coupler is detachably coupled to a drive mechanism for actuating reciprocal axial movement of the needle via the needle coupler. The drive mechanism may include a cam for translating a rotational motion into a reciprocal axial motion of the needle coupler.

DESCRIPTION OF ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

Figure 1:
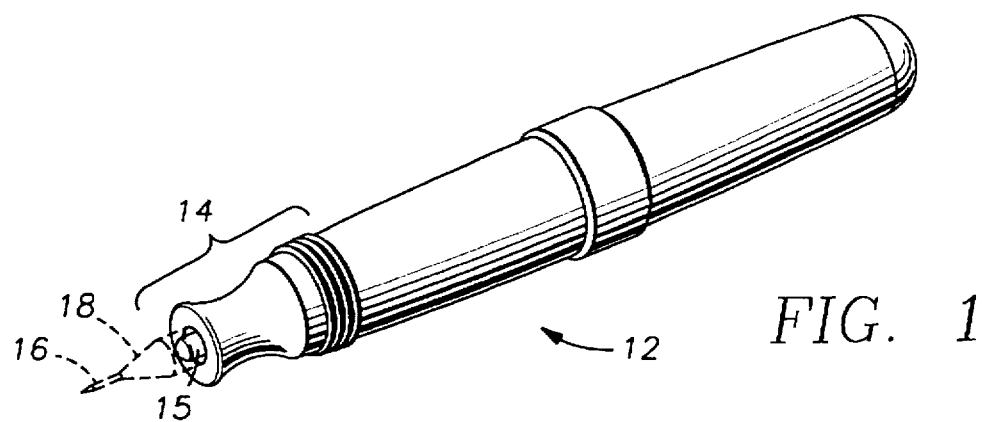
FIG. 1 is a perspective view of a pigment applicator device in accordance with one embodiment of the present invention.

FIG. 1 illustrates a pigment applicator device 10 in accordance with one embodiment of the present invention. In this particular embodiment, the device 10 includes an electro-mechanical means for actuating an applicator needle 16. It is understood that manual applicator device can also make use of the concept of the present invention without departing from the scope and spirit of the present invention as defined by the claims. The housing 12 of the device 10 is generally shaped like a fountain pen which provide a comfortable grip for the user. Specifically, the housing 12 includes a detachable finger grip section 14. The particular shape and size of the device housing may differ depending on the grip desired and the internal components of the device. A pigment applicator needle 16 is supported on the end of the grip section 14 by a needle support 18. The needle 16 is coupled to the device 10 by a detachable needle coupler 20 (hidden from view in FIG. 1, see FIGS. 2–7). Details of the mechanical construction of the device 10 and the interactive functions of the various parts are more apparent by reference to FIGS. 2–7 and the accompanying description below.

Figure 2:
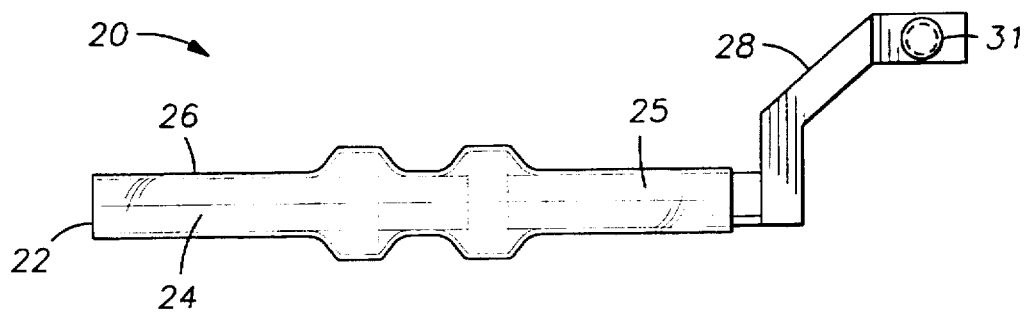
FIG. 2 is a side view of the needle coupler in accordance with one embodiment of the present invention.
Figure 3:
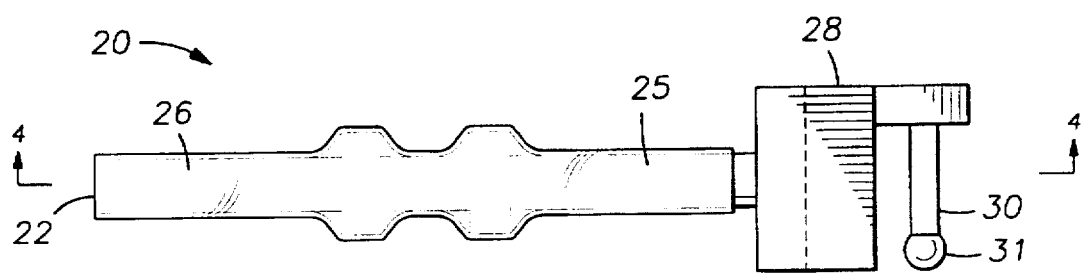
FIG. 3 is a top view of the needle coupler of FIG. 2.
Figure 4:
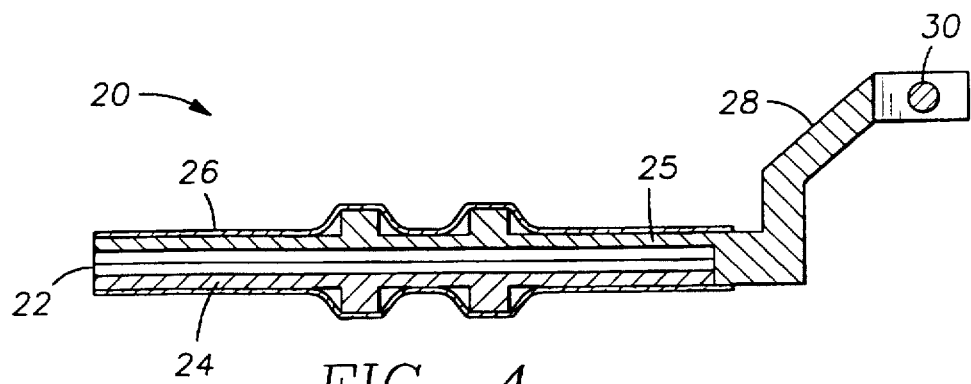
FIG. 4 is a sectional view taken along line 4—4 in FIG. 3.

Referring to FIGS. 2–4, details of the detachable needle coupler 20 in accordance with one embodiment of the present invention are described. The needle coupler has a generally cylindrical needle chamber 22 defined by two split sections 24 and 25 which are held together by a sleeve 26. The needle chamber 22 is sized to frictionally receive the metal needle 16 so that the needle 16 moves in unison with the chamber 22 during actuation of the needle coupler 20 as described below. The split sections 24 and 25 and sleeve 26 create a clamping action for a slightly oversized needle. The split section 25 is connected to an anchor section 28 shaped as shown in the figures. At the end of this anchor section 28 is a coupling pin 30 which axis is perpendicular to the axis of the needle chamber 22. This pin 30 has a slightly enlarged rounded end 31 and is for coupling to a rocker 42 (see FIG. 5).

Figure 5:
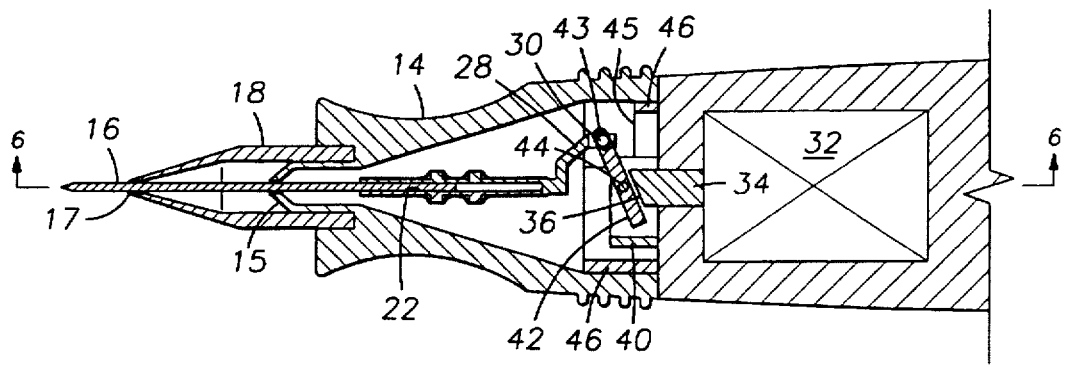
FIG. 5 is an axial sectional view of the device of FIG. 1.
Figure 6:
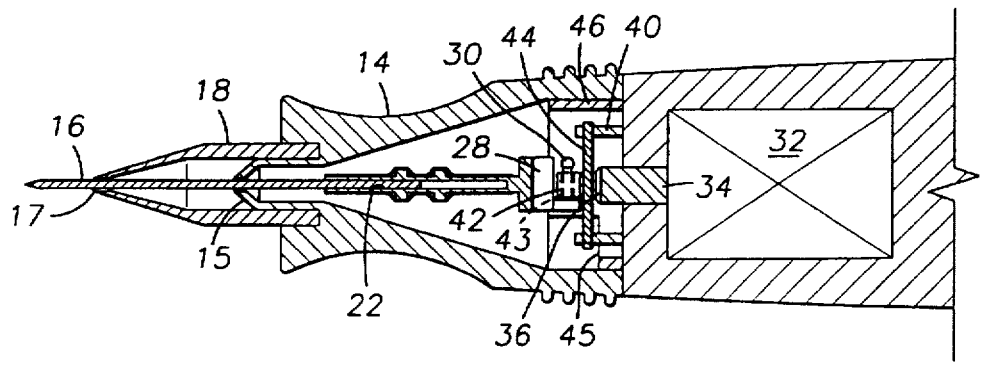
FIG. 6 is a sectional view taken along line 6—6 in FIG. 5 showing coupling of the needle coupler to the rocker (details of the surrounding components are omitted for clarity).
Figure 7:
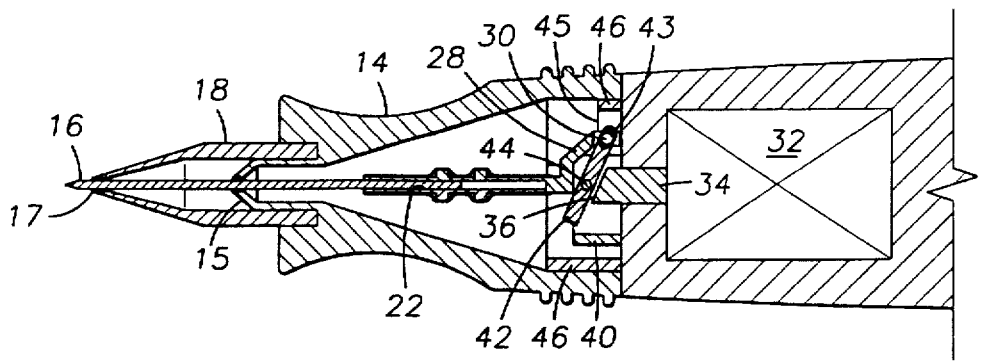
FIG. 7 is an axial sectional view of the device showing the retracted position of the needle coupler.

Referring now to FIGS. 5–7, the internal assembly of the device 10 is shown in detail. The grip section 14 is slidably and detachably attached to a flange 46 of the housing by interference or friction. The flange 46 has a slot 45 on one side large enough for the anchor section 28 of the needle coupler 20 to pass through it (this will become apparent later with the description below). Within the housing 12 is a suitable conventional drive such as a d.c. motor and associated drive collectively and schematically represented as structure 32. The specific type of drive can be selected accordingly to ordinary skill in the art to meet the intended functions disclosed herein. Power for the drive 32 may be supplied by an external power supply (not shown), build-in rechargeable battery (not shown) or alkaline battery (not shown).

The drive 32 rotates a shaft 34 which has a terminating flat cam surface 36 at an angle to the shaft axis. A rocker assembly 40 surrounds the shaft 34. The rocker assembly 40 includes a rocker 42 which is pivotally supported on a pivot pin 44 and at a point along the line of the axis of the shaft 34. The rocker 42 has an eye 43 at one end which axis is aligned parallel to the axis of the pivot pin 44. As the shaft 44 rotates, the cam surface 36 rocks the rocker 42 in a reciprocal motion in the axial direction of the shaft 34 and about the pivot pin 44.

The coupling pin 30 of the needle coupler 20 is pivotally coupled to the eye 43 of the rocker 42. Specifically, the coupling pin 30 is sized to freely rotate in the eye 43. However, the rounded end 31 of the coupling pin 30 is sized to provide an interference fit to allow the coupling pin 30 to be inserted into or withdraw from the eye 43 by applying a moderate force using the user's finger, but prevents the coupling pin 30 from loosening from the eye 43 during normal operation of the device. The needle coupler 20 extends inside of the grip section 14.

To use the device 10, the needle coupler 20 is first attached to the rocker assembly 40 by inserting the coupling pin 30 through the eye 43. The slot 45 in the flange 46 allows room for the sideways movement of the anchor section 28 of the needle coupler 20 when inserting the coupling pin 30 into the eye 43. The grip section 14 is then attached to the flange 46. The needle support 18 is attached to the stub 15 at the end of the grip section 14. The needle 16 is inserted through the clearance hole 17 in the needle support 18 and into the needle chamber 22. When power is turned on, the shaft 34 rotates and the cam surface 36 rocks the rocker 42 reciprocally in the axial direction of the shaft 34. The reciprocal rocking motion of the needle coupler 20 causes axial reciprocal motion of the needle 16 relative to the grip section 14 and needle support 18. FIG. 5 shows the needle 16 in its extreme extended position and FIG. 7 shows the needle 16 in its extreme retracted position. The needle support 18 and needle chamber 22 provide support to the thin needle 16 during its reciprocal axial motion. The perpendicular direction of the axis of the coupling pin 30 with respect to the direction of the axial reciprocal motion ensures positive coupling of the needle coupler 20 to the rocker 42, which prevents slippage of the needle coupler 20 with respect to the rocker 42 during repeated reciprocal axial motion.

After completing the tattooing procedure, the needle 16 and the grip section 14 are removed. The needle coupler can be removed from the rocker 42 by pulling the coupling pin 30 against the interference fit between the rounded end 31 and the eye 43. The slot 45 in the flange 46 allows room for the sideways movement of the anchor section 28 of the needle coupler 20 when withdrawing the coupling pin 30 from the eye 43.

It can be seen that the operations of attaching and detaching of the needle coupler do not require the use of any tool (e.g. a screw driver). A pair of tweezers may be desirable for handling a contaminated needle coupler, but it is not required for the purpose of making the physical attachment or detachment of the needle coupler to the rocker assembly.

By making the grip section 14 detachable from the rest of the housing 12 and the needle coupler 20 detachable from the drive mechanism, these parts when contaminated by blood from the tattooing procedure can be discarded or decontaminated by appropriate procedures. If meant to be disposable, the grip section 14 and the needle coupler 20 may be made of plastic to reduce their cost. These parts may be made of a material suitable for autoclaving or other acceptable decontamination procedure if they are to be reused.

While the invention has been described with respect to the embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

I claim:

1. A pigment applicator device comprising:
   a body portion;
   a drive mechanism contained substantially within the body portion;
   a needle; and
   a needle coupler that receives the needle at a first end and connects to the drive mechanism at a second end, the needle coupler having a needle chamber that receives the needle at the first end and an anchor section that detachably couples the needle coupler at the second end to the drive mechanism, wherein the anchor section is coupled to the drive mechanism with an interference fit and can be coupled and decoupled from the drive mechanism during normal operation.

2. A pigment applicator device as defined in claim 1, wherein the needle chamber is formed from split sections clamped together by a sleeve.

3. A pigment applicator device as defined in claim 1, wherein the needle coupler is constructed from a plastic material.

4. A pigment applicator device as defined in claim 1, wherein the needle chamber comprises a generally cylindrical portion.

5. A pigment applicator device as defined in claim 1, wherein the anchor section includes a coupling pin that is received by the drive mechanism and thereby detachably couples the anchor section to the drive mechanism with an interference fit.

* * * * *